United States Patent [19]

d'Orchymont et al.

[11] Patent Number: 5,106,861
[45] Date of Patent: Apr. 21, 1992

[54] METHOD OF USING CERTAIN TETRALIN DERIVATIVES TO PRODUCE ANALGESIC RELIEF

[75] Inventors: Hugues d'Orchymont; Celine Tarnus, both of Strasbourg, France

[73] Assignee: Merrell Dow Pharmaceuticals Inc., Cincinnati, Ohio

[21] Appl. No.: 704,156

[22] Filed: May 22, 1991

Related U.S. Application Data

[62] Division of Ser. No. 460,693, Jan. 4, 1990, Pat. No. 5,041,673.

[51] Int. Cl.$^5$ .............................................. A61K 31/41
[52] U.S. Cl. ..................................................... 514/360
[58] Field of Search ......................................... 514/360

Primary Examiner—S. J. Friedman
Attorney, Agent, or Firm—William J. Stein

[57] ABSTRACT

This invention relates to novel derivatives of tetralin, to the processes for their preparation, to their use as amino-peptidase inhibitors and to their end-use application as immunomodulators and as analgesic agents.

8 Claims, No Drawings

METHOD OF USING CERTAIN TETRALIN DERIVATIVES TO PRODUCE ANALGESIC RELIEF

This is a divisional of application Ser. No. 07/460,693, filed Jan. 4, 1990, U.S. Pat. No. 5,041,673.

This invention relates to novel derivatives of tetralin, to the processes for their preparation, to their use as aminopeptidase inhibitors and to their end-use application as immunomodulators and as analgesic agents.

More specifically this invention relates to 3-aminonaphthalene-2-one derivatives of the formula

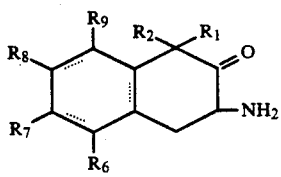

I the enantiomeric forms and mixtures thereof, and the pharmaceutically acceptable salts thereof wherein the dotted lines represent facultative double bonds, $R_1$ is H, F, Cl, $C_{1-6}$ alkyl, OH, $C_{1-6}$ alkoxy, $C_{1-6}$ alkyl thio, $C_{1-6}$ acylamino, or $C_{1-6}$ acyloxy, $R_2$ is H, Cl, F or $C_{1-6}$ alkyl, each of $R_6$, $R_7$, $R_8$ and $R_9$ is H, Cl, F, $C_{1-6}$ alkyl, $C_{1-6}$ alkylamino, $C_{1-6}$ alkoxy, aryl or aralkyl and when $R_6$ and $R_7$, $R_7$ and $R_8$, and $R_8$ and $R_9$ are taken together with the carbon atoms to which they are attached form a 5-6 membered carbocyclic moiety with the proviso that the number of so-formed carbocyclic moieties is limited to less than 3, and with the further proviso that when the depicted ring moiety having the facultative double bonds is saturated then any 5-6 membered carbocyclic moiety formed therewith is also saturated.

As used herein the term aryl includes phenyl which may be substituted with Cl, F, $C_{1-6}$ alkyl, $C_{1-6}$ alkoxy, $C_{1-6}$ alkylamino radicals but preferably is phenyl, the term aralkyl includes benzyl or phenethyl the phenyl moieties of which may optionally be substituted with Cl, F, $C_{1-6}$ alkyl, $C_{1-6}$ alkoxy or $C_{1-6}$ alkylamino moieties. preferably aralkyl being benzyl or phenethyl. The term $C_{1-6}$ alkyl thiol embraces those radicals $-S-C_{1-6}$ alkyl, the term $C_{1-6}$ acylamino embraces radicals of the formula $-NHC(O)R$ wherein R is H or $C_{1-6}$ alkyl, and the term $C_{1-6}$ acyloxy embraces radicals of the formula $-OC(O)R$ wherein R is H or $C_{1-6}$ alkyl. (The C(O) moiety represents a carbonyl function.) Included within the $C_{1-6}$ alkyl and other $C_{1-6}$ hydrocarboxy moieties are the straight and branched chain moieties, preferably methyl and ethyl. In general when the $R_6$ and $R_7$, $R_7$ and $R_8$, or $R_8$ and $R_9$ moieties form an additional ring, it is preferred that phenanthrenone moieties be formed, particularly at the $R_6$ and $R_7$ or at the $R_8$ and $R_9$ positions.

The term "pharmaceutically acceptable acid addition salts" is intended to apply to any non toxic organic or inorganic acid addition salt of the base compounds represented by Formula I. Illustrative inorganic acids which form suitable salts include hydrochloric, hydrobromic, sulphuric and phosphoric acid and acid metal salts such as sodium mono hydrogen orthophosphate and potassium hydrogen sulfate. Illustrative organic acids which form suitable salts include the mono, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophilic organic solvents, which in comparison to their free base forms, generally demonstrate higher melting points and an increased chemical stability.

Racemic mixtures of enantiomers may be resolved by standard procedures well known in the art and include such practices as fractional crystallization, chromatographic techniques and the use of chiral auxiliary reagents.

In general, the preparation of the compounds of this invention may be effected by chemical processes analogously known in the art. Of course, the choice of the pathway for the obtention of any specific compound depends on the number and type of substituents for the given compound, by the ready availability of the starting materials and such other factors well understood by the ordinarily skilled artisan.

In those instances wherein $R_1$, $R_2$, $R_6$, $R_7$, $R_8$ and $R_9$ moieties are hydrogen the compound is prepared from naphthalene wherein a Birch-type reduction to its 1,4-dihydronaphthalene analog (3). followed by an epoxidation reaction with m-chloroperbenzoic acid in acetonitrile yields 2,3 epoxy-1,2,3,4-tetrahydronaphthalene which, upon treatment with aqueous ammonia, yields trans3-amino-1,2,3,4-tetrahydro-2-naphthalenol (5). The amine is N protected preferably with a t-butyloxycarbonyl (BOC) although other protecting groups may similarly be sued, and the N-protected compound (6) is oxidized to its analogous ketone (7) according to standard procedures such as with pyridinium dichromate (PDC), or with Dess-Martin periodinane. The protecting group is removed by cleavage under acidic conditions or by hydrogenolysis using standard techniques well known in the art, e.g. using HCl, HBr, $H_2SO_4$ and the like, or hydrogenation in the presence of a catalyst, or by acid hydrolysis in an inert atmosphere (argon or nitrogen) to produce the desired 3-amino-3,4-dihydro-2(1H)-naphthalenone (8) (as a salt). This series of reactions is depicted in Reaction Scheme A.

REACTION SCHEME A

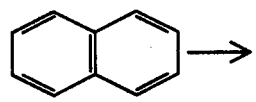

(2)

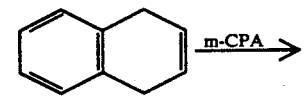

(3)

-continued
REACTION SCHEME A

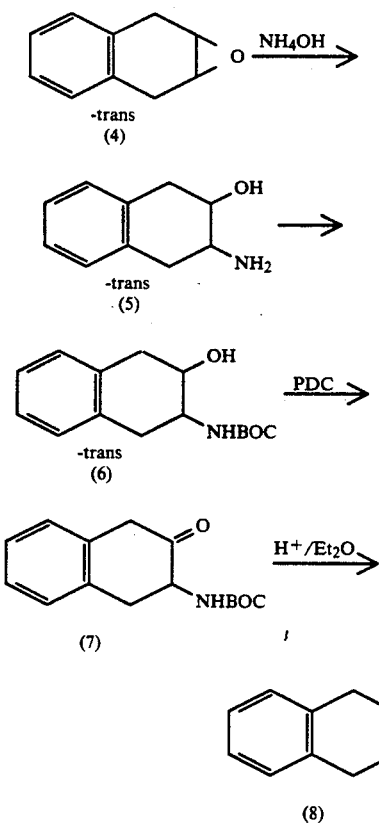

Optically active (+) and (−)- 3-amino-3,4-dihydro2-(1H)-naphthalenones are synthetized according to Scheme A wherein racemic trans 3-amino-1,2,3,4-tetrahydro 2-naphthalenol is resolved via the formation of diastereoisomeric phenylpropionyl amides. For example, racemic trans-3-amino 1,2,3,4-tetrahydro-2-naphthalenol is coupled with R-(−)-2-phenyl-propionic acid to produce 2 diastereoisomeric amides (9) and (10) which are readily separated by chromatography on silica gel using standard techniques. The chiral auxiliary group is then removed by hydrolytic cleavage in aqueous HCl and the resulting optically active 3-amino-1,2,3,4-tetrahydro-2-naphthalenols are converted to their BOC-amino derivatives, oxidized and deprotected as described for the general reactions of Scheme A. The two diastereoisomeric amides are of the formulae

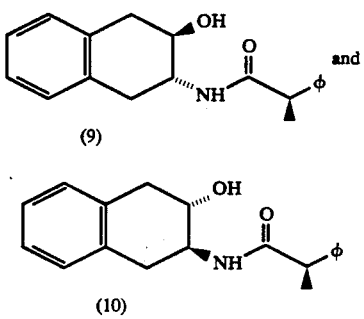

wherein φ represents phenyl.

In those instances wherein the $R_6$–$R_9$ substituents are other than hydrogen, alternate routes of synthesis are required using intermediates which are suitable for a variety of synthetic pathways. It is convenient to utilize the appropriately $R_6$, $R_7R_8$, $R_9$ substituted benzaldehydes as starting materials for conversion to the desired intermediates (i.e, N-protected-α, α-diethoxymethyl-β-aminopropanol derivatives (16) of the $R_6$–$R_9$ substituted benzaldehydes). In this synthetic approach, the $R_6$–$R_9$ benzaldehydes are generally commercially available compounds, but in those instances wherein any particular benzaldehyde or naphthalene aldehyde is not available it may be prepared by techniques analogously known in the art. The preparation of the intermediates is summarized by the depiction of the following scheme.

REACTION SCHEME B

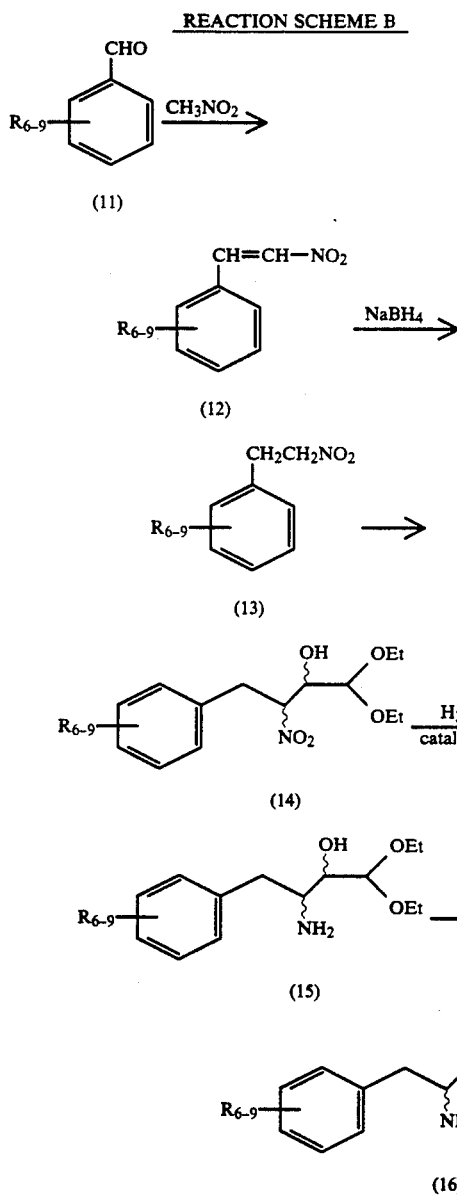

wherein the wavy lines of the compounds of Formulae 14 to 16 designate that these groups can be in either the R or the S configurations, "$R_{6-9}$" is a short-hand composite of the $R_6$, $R_7$, $R_8$ and $R_9$ substituents (representing mono-, multi-, or non-substituted intermediates as the $R_6$, $R_7$, $R_8$ and $R_9$ substituents are shown and defined for Formula I), Pg represents a nitrogen protecting group and Et represents ethyl.

The foregoing scheme involves the conversion of the aldehyde (11) to its nitroethenyl derivative (12) by treatment with nitromethane, in the presence of ammonium acetate. The reaction takes place in acetic acid under reflux conditions for about 2-6 hours. The nitroethenyl moiety is reduced, preferably with sodium borohydride (although other reducing agents may similarly be used) and the so-reduced compounds (13) are reacted with a monodialkylacetal of glyoxal (preferably monodiethylacetal of glyoxal) using a basic catalyst (preferably potassium carbonate) at about 50° C. in an inert atmosphere (argon or nitrogen) for about 1 to 4 hours to yield a compound (14) bearing an α,α, -diethoxymethyl-β-nitropropanol moiety. The resulting intermediates are chemically reduced, preferably in a closed system under atmospheric pressure or under pressure (50-70psi) by reaction with hydrogen in the presence of Raney nickel using isopropanol as solvent. The resulting amino moiety is protected with a suitable protecting group, preferably using di-t-butyldicarbonate or benzylchloroformate (producing BOC or CBZ protecting groups respectively). In each of the foregoing steps standard procedures and methodology well known to the person of ordinary skill in the art are utilized. At this juncture in the synthesis toward the obtention of the desired compounds of Formula I, it is convenient to separate diastereomeric pairs of enantiomers. In general such separation may be effected by standard techniques well known in the art. For example using chromatographic techniques, sequential elution from silica gel with varying concentrations of solvent mixtures, and fractional crystallization will afford separation of the diastereomeric forms.

The preparation of compounds of Formula 20, wherein $R_1$ and $R_2$ are hydrogen, may conveniently be effected by the procedures depicted in the following reaction scheme.

REACTION SCHEME C

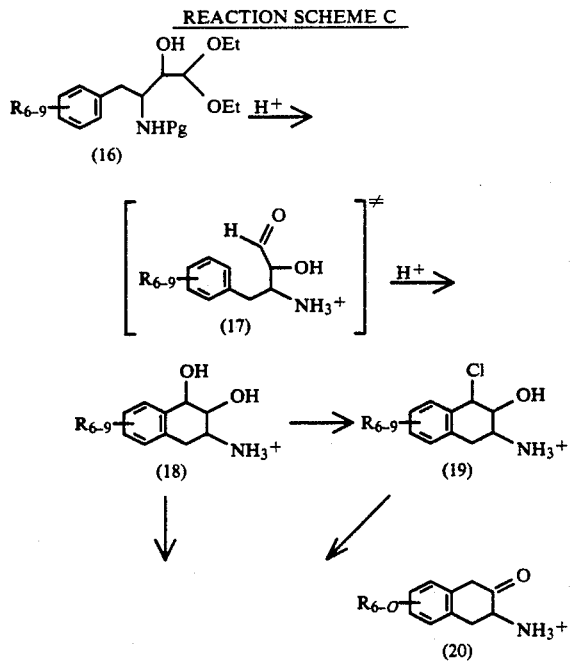

The foregoing Reaction Scheme C involves the treatment of the N-protected amino hydroxy acetals (16)

with strong acids, the choice of acid depending on the route of synthesis desired and/or whether or not the $R_{6-9}$ substituents are electron donating. For example, treatment of compounds 16 with 37% HCl at temperatures of about 80-100° C. for 2 to 10 minutes produces 3-amino-1,2,3,4--tetrahydro-1,2-naphthalenediols (18) via an internal Friedel Crafts type alkylation of the amino hydroxy aldehydes of Formula 17 or the 3-amino-1--chloro-1,2,3,4-tetrahydronaphthalenol intemediates (19), formed via an $S_N1$-type reaction of chloride ions, which are warmed under acidic conditions to effect a Pinacol rearrangement to produce compounds 20. Alternatively, compounds 20 may be produced directly by refluxing the N-protected hydroxy acetals (16) with trifluoro acetic acid for about 2-5 hours. Still another method for producing the compounds 20 is by treating those intermediates of Formula 16 bearing electron donating groups (e.g., alkoxy and alkylamino) with hydrochloric acid for about 2-10 minutes at about 80-100° C.

In those instances wherein it is desired to prepare final compounds wherein $R_1$ and $R_2$ are hydrogen and the Pinacol rearrangement is not preferred, compounds (18) and (19) may be chemically reduced using standard hydrogenation procedures such as by treatment with hydrogen in the presence of a catalyst. The resulting 2-hydroxy-3-amino compounds are N-protected, oxidized and deprotected as described above.

The compounds (18) and (19) are also useful intermediates to introduce a functional group at the 1-position and thus have access to compounds of Formula I wherein $R_1$ is H and $R_2$ is fluoro, chloro. alkyl, alkoxy or alkylamino, or wherein $R_1$ and $R_2$ are both halogen. This set of reactions is illustrated by Reaction Scheme D.

REACTION SCHEME D

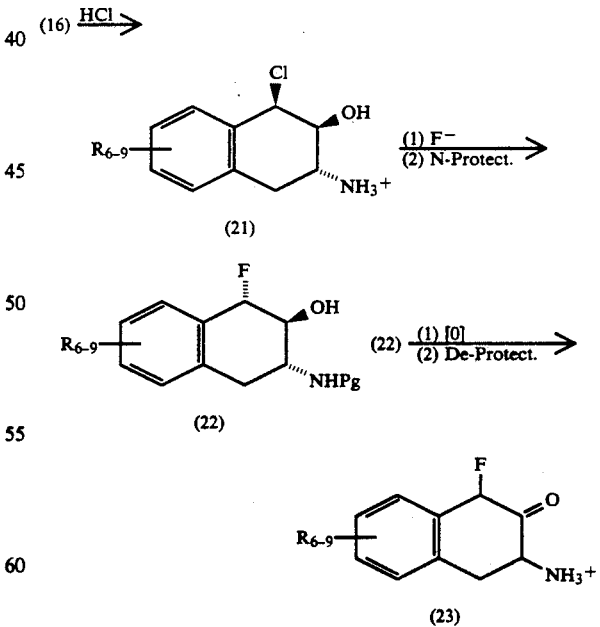

Reaction Scheme D is initiated by an intramolecular chloroalkylation reaction by treating compounds (16) with 37% aqueous HCl at 80-100° C. for 2 to 5 minutes (typically 3 minutes) to form 3-amino-1-chloro-1,2,3,4-tetrahydro-2-naphthalenol derivatives (21). Since the starting material, compounds (16) has two chiral centers, it consists of two pairs of enantiomers which are diastereoisomeric that are resolved using standard techniques. Starting from the suitable enantiomers pair, the foregoing process results in the production of cis-chlorohydrin (i.e., the chloro substituent and the hydroxyl function are in a cis relationship). Following the intramolecular chloroalkylation reaction the amino function is protected with an acid labile protecting group (preferably with a BOC protecting group). The N-protected cis-chlorohydrin is subjected to a replacement reaction using a fluoride ion source reactant. For the conversion of cis-chlorohydrin to the corresponding trans-fluorohydrin it is preferred to utilize a polymeric ion resin (e.g., Amberlyst A-26F) wherein the reactants are refluxed in an appropriate solvent. Of course, other fluoro ion source may similarly be used [e.g., tetrabutylammonium fluoride ($Bu_4NF$), cesium fluoride or potassium fluoride]. Following fluorination the resulting trans fluorohydrins (22) are oxidized to the fluoro ketones and deprotected in acid media to form the 1-fluoro-3-amino-3,4-dihydro-2(1H)-naphthalenones of Formula 23.

An alternate procedure to the obtention of 1-fluoro-3-amino-3,4-dihydro2(1H)-naphthalenones is illustrated in the following scheme:

REACTION SCHEME E

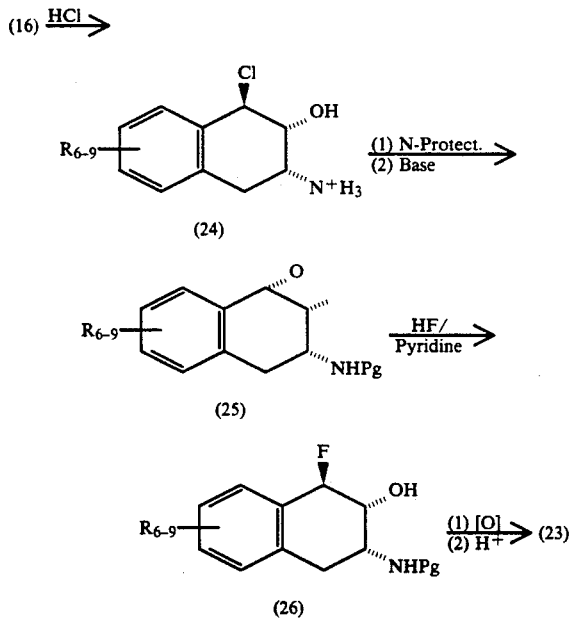

The alternate procedure for the preparation of the 1-fluoro compounds of Formula 18 is initiated by N protecting the trans-chlorohydrins (24), (formed by reaction of the suitable enantiomers pair of compounds (16) with HCl) followed by treatment of the N-protected trans-chlorohydrins with a base, preferably with 1,8-diazobicyclo[5.4.0]undec7-ene (DBU) in a suitable solvent (tetrahydrofuran) under reflux followed by treatment of the resulting 2,3-epoxides (25) with 70% HF/pyridine (diluted in an appropriate solvent, e.g., diethyl ether) to produce fluorohydrins (26) which are oxidized and N-deprotected (as previously described) to produce the desired 1-fluoro3-amino-$R_{6-9}$-substituted 3,4-dihydro-2(1H)-naphthalenones (23).

Similarly, reaction of the N protected cis-chlorohydrins of Formula 21 with the appropriate primary amine (i.e.,$RNH_2$ wherein R is alkyl) in an aprotic solvent (e.g., tetrahydrofuran) yields the 1-alkylamino-3-N-protected amine 1,2,3,4-tetrahydro-2-naphthalenols which, following the N-protection of the 1-position alkylamino, oxidation and deprotection steps, yields the desired 3-amino-1-aminoalkyl-3,4-dihydro-2(1H)naphthalenones.

To prepare compounds wherein $R_1$ is H and $R_2$ is alkoxy, the epoxides of Formula 25 are treated with an alcohol in the presence of a Lewis acid (e.g., titanium (IV) isopropoxide) to produce 1-alkoxy analogs of compounds 26 and these are oxidized and N-deprotected to produce the desired 1-alkoxy-3-amino-3,4-dihydro-2(1H)naphthalenones of Formula I. Similarly, to produce compounds of Formula I wherein $R_1$ is H and $R_2$ is alkyl, the epoxides of Formula 25 are reacted with an appropriate organometallic reactant (e.g., a Grignard reagent, cuprate, organolithiums, organoalanes, organo zincs) according to standard techniques to produce the 1-alkyl-3-amino-3,4-dihydro-2-naphthalenones of Formula I.

In those instances wherein it is desired to prepare compounds of Formula I wherein $R_1$ and $R_2$ are both fluoro, cischlorohydrins (21) are acylated to form corresponding benzoylamides (using benzoyl chloride) and these amides are treated with thionyl chloride to form an oxazole, (i.e., a compound of Formula 27

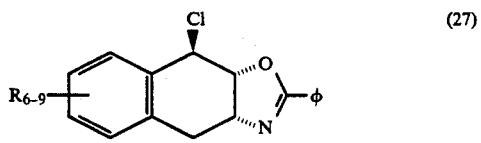

wherein $\phi$ represents phenyl), which is sequentially treated with lithium hydroxide in a methoxyethanol/water mixture and the resulting alcohol is oxidized to its corresponding 1-keto analog. The ketone is treated with diethylaminosulfur trifluoride (DAST) to yield the corresponding 1,1-difluoro analogs of compounds of Formula 27. Treatment with aqueous acid hydrolizes off the oxazole moiety to produce the desired 1,1-difluoro-1,2,3,4-tetrahydro-2-naphthalenols which are N-protected, oxidized and N-deprotected to their corresponding ketones of Formula I. All of these foregoing reactions use procedures analogously known in the prior art.

In those instances wherein it is desired to prepare compounds not having any aromatic ring system nor having any reducible functions, it is generally preferred to reduce any aromatic ring prior to oxidation of the 2-hydroxy function to its ketone. Preferably the compounds are hydrogenated under pressure (60 to 70 psi) in acetic acid over platinium oxide at room temperature. The resulting compounds are converted to compounds of Formula I according to the foregoing chemistry.

REACTION SCHEME F

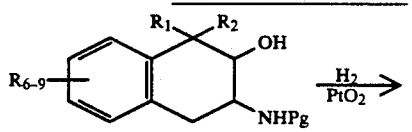

-continued
REACTION SCHEME F

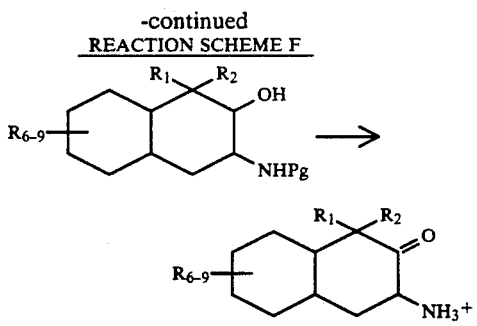

The preparation of compounds wherein $R_1$ is a thiol may be accomplished by reacting a 2,3-epoxide intermediate with a sodium thiolate in tetrahydrofuran according to standard reaction conditions. Similarly, using standard acylation procedures, such as reaction of a 1—OH intermediate with an acid chloride or anhydride, the 1-position acyloxy analogs may be formed, and by reacting a 1-position amine with an acid chloride or anhydride using standard procedures will effect acylamination. Following such reactions the compounds may be converted to the desired final products of Formula I by using the techniques herein described and exemplified.

In general the foregoing reactions all use processes and techniques analogously described in the art. These processes, as adopted for the particular compounds of this invention, are described by the following specific examples.

EXAMPLE 1

3-Amino-3,4-dihydro-2-(1H)-naphthalenone, hydrochloride

Step A: 2,3-Epoxy-1,2,3,4-tetrahydronaphthalene

A solution of metachloroperbenzoic acid (55%, 22.8 g) in acetonitrile (190 ml) was added dropwise over 15 min to a solution of 1,4 dihydro naphthalene (7.86 g) in acetonitrile (100 ml) at 0° C. The resulting mixture was stirred for 6 hours at room temperature. The mixture was concentrated to about 50 ml under reduced pressure, diluted with methylene chloride and filtered. The filtrate was washed with 10% aqueous sodium sulfite, saturated aqueous sodium hydrogenocarbonate, saturated aqueous sodium chloride, dried over magnesium sulfate and concentrated in vacuo. The resulting solid (8.45 g) was chromatographed (silica gel, 150 g, elution with ethyl acetate:hexane, 1:9) to give the title compound as a solid (5.81 g).

Step B: Trans 3-tert-butoxycarbonylamino-1,2,3,4-tetrahydro-2-naphthalenol

A suspension of 2,3-epoxy1,2,3,4-tetrahydronaphthalene (5.66 g) in 25% aqueous ammonia (100 ml) was warmed in a bomb at 100° C. for a period of 4 hours. The mixture was evaporated under reduced pressure and the residue was treated with a solution of di-tert-butyl-dicarbonate (8.18 g) in methanol (100 ml). After stirring overnight the mixture was concentrated in vacuo. Recrystallization of the residue from a chloroform/hexane mixture yielded 6.12 g of the title compound as a white solid, m.p. 149–150° C.

Step C:
3-Tert-butoxycarbonylamino-3,4-dihydro-2(1H)-naphthalenone

Under argon to a solution of trans 3 tert-butoxycarbonylamino 1,2,3,4-tetrahydro-2-naphthalenol (2.02 g) in methylene chloride (40 ml) was added pyridinium dichromate (4.3 g), molecular sieves 3A (6.3 g) and acetic acid (0.76 ml). After 1 hour stirring at room temperature the mixture was poured on a silica gel column (120 g, elution with ethyl acetate: cyclohexane, 1:3) to afford a crude material which was recrystallized from a diethyl ether/cyclohexane mixture to give the title compound (634 mg) as a white solid, m.p. 104–105° C.

Step D: 3-Amino3,4-dihydro-2-(1H)-naphthalenone, hydrochloride

Under argon 3-tert-butoxycarbonylamino-3,4-dihydro-2(1H)-naphthalenone (623 mg) was dissolved in diethyl ether (20 ml). A saturated solution of hydrochloric acid in diethyl ether (16.5 ml) was then added. Stirring at room temperature was maintained for 1 hour. The precipitate was filtered and dried in vacuo to yield the title compound (408 mg) as a white solid, m.p. 163° C. (dec.).

PREPARATION OF PURE ENANTIOMERS OF 3-Amino-3,4-dihydro2-(1H)-naphthalenone, hydrochloride

EXAMPLE 2

(+)-3-Amino-3,4-dihydro-2(1H)-naphthalenone, hydrochloride

Step A:
Trans-N-[(2R)-2-phenylpropanoyl]-3-amino-1,2,3,4-tetrahydro-2-naphthalenol, diastereoisomer A and diastereoisomer B Under argon to a solution of R-(—)-2-phenylpropionic acid (505 mg) in methylene chloride (10 ml) at 0° C. was added hydroxybenzotriazole, hydrate (530 mg) and dicyclohexylcarbodiimide (718 mg). The mixture was stirred at 0° C. for 10 minutes before addition of racemic trans-3-amino-1,2,3,4-tetrahydro-2-naphthalenol, hydrochloride (723 mg) and N-methylmorpholin (438 mg) in methylene chloride (5 ml). Stirring was maintained at 0° C. for 3 hours and at room temperature overnight. The reaction mixture was diluted with ethyl acetate and filtered. Evaporation of solvent gave the crude mixture of diastereoisomer A and diastereoisomer B. The diastereoisomer separation was achieved by chromatography on silica gel [160 g, elution with ethyl acetate: cyclohexane, 1:9 (700 ml), 2:8 (1 l), 3:7 (1 l) 2:3 (1 l) and 1:1 (1 l)]. Diastereoisomer A obtained as a white solid (232 mg) was recrystallized in ethyl acetate/cyclohexane, m.p. 158° C., Rf=0.30 (silica gel, ethyl acetate:cyclohexane, 1:1). Diastereoisomer B was recovered as a white solid (250 mg) and recrystallized in ethyl acetate, m.p. 179–180° C., Rf=0.40 (silica gel, ethyl acetate:cyclohexane, 1:1).

Step B:
(+)-Trans-3-amino-1,2,3,4-tetrahydro2-naphthalenol, hydrochloride

Trans-N-[(2R)-2-phenylpropanoyl]-3-amino-1,2,3,4-tetrahydro-2-naphthalenol, diastereoisomer A (183 mg) was refluxed in 6N aqueous hydrochloric acid (20 ml) for 4 hours. The reaction mixture was evaporated in vacuo and the residue taken up in water. The aqueous solution was washed with ethyl acetate and evaporated to give a white solid which was recrystallized from a methanol/ethyl acetate mixture to yield the title compound (99 mg).

Step C:
(+)-Trans-3-tert-butoxycarbonylamino-1,2,3,4-tetrahydro-2-naphthalenol

To (+)-trans-3-amino-1,2,3,4-tetrahydro-2-naphthalenol, hydrochloride (94 mg) was added a solution of di-tert-butyldicarbonate (110 mg) in methanol (1.5 ml) and a solution of triethylamine (59 mg) in methanol (1.5 ml). The reaction mixture was stirred for 1 hour at room temperature and evaporated in vacuo. The residue was taken up in methylene chloride, washed with water and saturated aqueous sodium chloride and dried over magnesium sulfate. Evaporation of solvent gave a crude material which was crystallized from a cyclohexane/ethyl acetate mixture to yield the title compound as a white solid (74 mg), m.p. 168–169° C.

Step D:
(+)-3-Tert-butoxycarbonylamino-3,4-dihydro-2(1H)-naphthalenone

Under argon to (+)-trans-3-tert-butoxycarbonylamino-1,2,3,4-tetrahydro-2-naphthalenol (70 mg) in methylene chloride (1 ml) was added Dess Martin periodinane (172 mg). The mixture was stirred for 1 hour at room temperature under argon and filtered through a silica gel column [10 g, elution with ethyl acetate: cyclohexane mixtures, 1:9 (150 ml) and 2:8 (50 ml)]. Evaporation of solvent gave a solid which was recrystallized from pentane to yield the title compound as white needles, m.p. 76° C.

Step E:
(+)-3-Amino-3,4-dihydro-2(1H)-naphthalenone, hydrochloride

The BOC protecting group of (+)-3-tert-butoxycarbonylamino-3,4-dihydro-2(1H)-naphthalenone (27 mg) was cleaved according to the procedure described in Example 1 step D to yield the title compound as a white amorphous solid (15 mg).

EXAMPLE 3

2-Amino-1,2-dihydro-3(4H)-phenanthrenone, trifluoroacetate

2-Amino-1,2-dihydro-3(4H)-phenanthrenone, hydrochloride

Step A: 2-(2-Nitroethenyl)naphthalene

A mixture of 2-naphthaldehyde (12 g), nitromethane (13.8 g) and ammonium acetate (5 g) in acetic acid (50 ml) was refluxed for 2½ hours. The brown mixture was poured into ice-water (100 ml) from which a yellow solid separated. Filtration and drying in vacuo afforded the title compound (14.4 g).

Step B: 2-(2-Nitroethyl)naphthalene

To a suspension of sodium borohydride (4 g) in a mixture of dioxane (85 ml) and ethanol (30 ml) was added dropwise a solution of 2-(2-nitroethenyl)naphthalene (100 g) in dioxane (90 ml) over 30 minutes. The flask was cooled with a cold water bath during addition. Stirring was maintained for an additional 1½ hours. Ice (100 ml) and 50% aqueous acetic acid (12 ml) were added and the mixture was stirred for 2 hours at room temperature, concentrated in vacuo and extracted with methylene chloride. The organic layer was washed with water, saturated aqueous sodium chloride and dried over magnesium sulfate. The solvent was evaporated in vacuo to yield an oil which was crystallized from acetic acid to give the title compound (6.79 g) as a yellow solid, m.p. 59–60° C.

Step C:
α,α-Diethoxymethyl-β-nitro-2-naphthalenepropanol

A mixture of 2-(2-nitroethyl)naphthalene (6.79 g), glyoxal monodiethylacetal (2.23 g) and potassium carbonate (0.26 g) was stirred at 50° C. under argon for 2 hours. The mixture was diluted with diethyl ether (50 ml) and water (50 ml) was added. The aqueous layer was extracted with diethyl ether (3×20 ml) and the combined organic solutions were washed with saturated aqueous sodium chloride (50 ml) and dried over magnesium sulfate. Evaporation of solvent yielded a residue which was chromatographed [silica gel 300 g, elution with cyclohexane:ethyl acetate, 9:1 (2 1) and with cyclohexane:ethyl acetate, 8:2 (2 1)]to give the title compound (4.72 g) as a brown oil. Step D: α,α-Diethoxy-β-tert-butoxycarbonylamino-2-naphthalenepropanol A mixture of α,α-diethoxymethyl-β-nitro-2-naphthalenepropanol (4.7 g) and Raney nickel in isopropanol (80 ml) was stirred under hydrogen at atmospheric pressure. When absorption of hydrogen was complete the mixture was degased in vacuo for 15 minutes and filtered through celite. Evaporation of the solvent in vacuo yielded α,α-diethoxymethyl-β-amino-2-naphthalenepropanol (3.69 g) as an oil.

A solution of α,α-diethoxymethyl-β-amino-2-naphthalenepropanol (3.62 g) in methanol (15 ml) was treated with di-tert-butyl-dicarbonate (2.68 g). The mixture was stirred for 1½ hours at room temperature, evaporated and the residue was chromatographed [silica gel 300 g, elution with cyclohexane:ethyl acetate, 9:1 (1.5 1), 2:8 (2 1) and 7:3 (1 1)]. Two isomers of the title compound were isolated, isomer A (1.57 g) as a yellow oil and isomer B (0.68 g) which could be crystallized from pentane to give the title compound as a white solid, m.p. 87° C. Rf isomer A=0.39, Rf isomer B=0.27 (silica gel, cyclohexane:ethyl acetate, 4:1).

Step E:
(+)-(2R,3S,4R)-2-Amino-4-chloro-1,2,3,4-tetrahydro-3-phenanthrenol, hydrochloride α,α-Diethoxy-β-tert-butoxycarbonylaminonaphthalenepropanol isomer A (239 mg) was stirred in 37% aqueous hydro chloric acid (10 ml) at 0° C. for 45 minutes and at 100° C. for 3 minutes. The flask was cooled with an ice water bath and the precipitate was filtered, washed with water and dried in vacuo to give the title compound (113 mg) as a white solid.

Step F:
(±)-(2R,3R,4R)-2-Amino-4-chloro-1,2,3,4-tetrahydro-3-phenanthrenol, hydrochloride α,α-Diethoxy-β-tert-butoxycarbonylaminonaphthalenepropanol isomer B (208 mg) was stirred in 37% aqueous hydrochloric acid (10 ml) at 0° C. for 2 hours and at 100° C. for 3 minutes. The flask was cooled with an ice water bath and the precipitate was filtered, washed with water and dried in vacuo to give the title compound (80 mg) as a white solid.

Step G:
(±)-2-Amino-1,2-dihydro-3(4H)-phenanthrenone, trifluoroacetate

2-Amino-4-chloro-1,2,3,4-tetrahydro-3-phenanthrenol, hydrochloride (40 mg) was refluxed in trifluoroacetic acid (17 ml) for 3½ hours. The solvent was removed in vacuo and the residue was crystallized from a cyclohexane/ethyl acetate mixture to yield the title compound (17 mg) as a cream-colored powder.

Step H:
(±)-2-Amino-1,2-dihydro-3-(4H)-phenanthrenone, hydrochloride

2-Amino-4-chloro-1,2,3,4-tetrahydro-3-phenanthrenol, hydrochloride (265 mg) was refluxed in trifluoroacetic acid (25 ml) for 3 hours. The green mixture was evaporated in vacuo taken up into methanol and treated with activated charcoal for 2 hours at room temperature. Filtration and evaporation yielded a yellow oil which was diluted with methanol and acidified with a solution of hydrochloric acid in diethyl ether. The mixture was evaporated and the acidification process was repeated. Evaporation gave a residue which was recrystallized in a methanol/diethyl ether mixture to afford the title compound (122 mg) as a cream colored powder.

EXAMPLE 4
2-Amino-1,2-dihydro-3(4H)-phenanthrenone, hydrochloride (alternative synthetic route)

Step A:
Trans-2-amino-1,2,3,4-tetrahydro-3-phenanthrenol, hydrochloride

A solution of (±)-(2R,3S,4R)-2-amino-4-chloro-1,2,3,4-tetrahydro-3-phenanthrenol hydrochloride (396 mg) in methanol (50 ml) was hydrogenated over 10% palladium on charcoal (109 mg) under atmospheric pressure at room temperature. When the theoretical amount of hydrogen was absorbed, the catalyst was filtered and the solvent evaporated under vacuum to give the title compound as a solid (315 mg).

Step B:
Trans-2-terbutoxycarbonylamino-1,2,3,4-tetrahydro-3-phenanthrenol

To a suspension of trans-2-amino-1,2,3,4-tetrahydro-3-phenanthrenol hydrochloride (315 mg) and diterbutyl dicarbonate (308 mg) in methanol (5 ml) was added dropwise a solution of triethylamine (153 mg) in methanol (5 ml). The resulting mixture was stirred for 1½ hours at room temperature and concentrated under vacuum. Water was added to the residue and the mixture was extracted with ethyl acetate. The organic layer was washed with saturated aqueous sodium chloride and dried over magnesium sulfate. Evaporation of solvents yielded the crude title compound (0.42 g) which was purified by chromatography on silica gel [100 g, elution with ethyl acetate:cyclohexane, 1:9 (0.5 1), 1:4 (1 1) and 3:7 (0.7 1)]. Evaporation of solvents yielded the title compound as a yellow solid (245 mg).Recrystallization in an ethyl acetate/cyclohexane mixture yielded pure trans-2-terbutoxycarbonylamino-1,2,3,4-tetrahydro-3-phenanthrenol as a white solid (183 mg).

Step C: 2-tertbutoxycarbonylamino-1,2-dihydro-3(4H)-phenanthrenone

Under argon to a solution of trans-2-tertbutoxycarbonyl-amino-1,2,3,4-tetrahydro-3-phenanthrenol (140 mg) in anhydrous methylene chloride (5 ml) was added Dess-Martin periodinane (281 mg). Agitation was maintained for 1 hour at room temperature and the reaction mixture was filtered on silica gel (30 g, elution with ethyl acetate:cyclohexane, 1:9). Evaporation of solvents gave the crude title compound (136 mg) which was recrystallized from a pentane/ethyl acetate mixture. The title compound was obtained as white needles (89 mg).

Step D: 2-amino-1,2-dihydro-3(4H)-phenanthrenone, hydrochloride

Under argon to a solution of 2-tertbutoxycarbonylamino-1,2-dihydro-3(4H) -phenanthrenone (74 mg) in anhydrous diethyl ether (5 ml) was added a saturated solution of hydrochloric acid in diethyl ether (5 ml). The mixture was stirred for 6 hours and the formed precipitate was filtered and dried under vacuum to afford the title compound as a white solid (42 mg)

EXAMPLE 5
3-Amino-3,4-dihydro-2(1H)-phenanthrenone, hydrochloride

Step A: 1-(2-Nitroethenyl)naphthalene

1-Naphthaldehyde (20 g) was treated according to the procedure in Example 3 step A. The crude compound was recrystallized from acetic acid to yield the title compound (16.1 g) as a yellow solid.

Step B: 1-(2-Nitroethyl)naphthalene 1-(2-Nitroethenyl)naphthalene (16.1 g) was reduced to the title compound according to the procedure described in Example 3 Step B. The crude product was crystallized from a methylene chloride/cyclohexane mixture to give the title compound (6.27 g) as a yellow solid. The crystallization residue was chromatographed (silica gel, elution with cyclohexane:ethyl acetate, 95:5) and the purified product was recrystallized from pentane/diethyl ether to yield the title compound (6.1 g) as white needles, m.p. 45–46° C.

Step C:
α,α-Diethoxyethyl-β-nitro-1-naphthalenepropanol

A mixture of 1-(Z-nitroethyl)naphthalene (12.2 g), glyoxal monodiethylacetal (3.98 g) and potassium carbonate (0.42 g) was stirred under argon at 50° C. for 1¾ hours. The mixture was diluted with diethyl ether (100 ml) and water (100 ml) was added. The aqueous layer was re extracted with diethyl ether (3×30 ml) and the combined organic solutions were washed with saturated aqueous sodium chloride (100 ml) and dried over magnesium sulfate. Evaporation of solvent in vacuo gave a residue which was chromatographed [silica gel, 330 g, elution with ethyl acetate:cyclohexane, 1:9 (3 1) and 2:8 (2.5 1)]. After evaporation of solvents the title compound (7.76 g) was obtained as a yellow oil.

Step D:
α,α-Diethoxymethyl-β-tert-butoxycarbonylamino-1-naphthalenepropanol

A mixture of α,α-diethoxymethyl-β-nitro-1-naphthalenepropanol (7.75 g) and Raney nickel (0.8 g) in isopropanol (100 ml) was stirred under hydrogen at atmospheric pressure until hydrogen absorption stopped. The mixture was then degased for 15 minutes in vacuo and filtered through celite. The filtrate was evaporated in vacuo to yield α,α-diethoxymethyl-β-amino-1-naphthalenepropanol (6.37 g) as an oil.

A solution of α,α-diethoxymethyl-β-amino-1-naphthalenepropanol (6.37 g), di-tert-butyl dicarbonate (4.73 g) in methanol (120 ml) was stirred at room temperature for 1¾ hours. The mixture was concentrated under reduced pressure and the residue was chromatographed [silica gel 280 g, elution with ethyl acetate:cyclohexane, 1:9 (1 1) and 2:8 (3 1)]. Two isomers of the title compound were isolated as oils, isomer A (3.15 g) and isomer B (2.81 g). Rf isomer A=0.52, Rf isomer B=0.45 (silica gel, ethyl acetate:cyclohexane, 1:1). These oils could be crystallized from pentane. m.p. isomer A 93° C., isomer B 102° C.

Step E:
(±)-(1S,2R,3S)-3-Amino-1-chloro-1,2,3,4-tetrahydro-2-phenanthrenol, hydrochloride A suspension of α,α-diethoxymethyl-β-tert-butoxycarbonylamino-1-naphthalenepropanol (250 mg), isomer A was stirred in 37% aqueous hydrochloric acid at 0° C. for 1 hour. The resulting emulsion was then stirred at 100° C. for 3 minutes and the flask was immediately cooled in an ice water bath. The precipitate was filtered, washed with water and dried in vacuo to yield the title compound (152 mg) as a white solid.

(±)-(1S,2S,3S)-3-Amino-1-chloro-1,2,3,4-tetrahydro-2-phenanthrenol, hydrochloride A suspension of α,α-diethoxymethyl-β-tert-butoxycarbonylamino-1-naphthalenepropanol (252 mg), isomer B was stirred in 37% aqueous hydrochloric acid at 0° C. for 50 minutes. The resulting suspension was then stirred at 100° C. for 3 minutes. The reaction flask was cooled at 0° C. and the precipitate was filtered, washed with water and dried in vacuo. The title compound (156 mg) was obtained as a white solid.

Step F: 3-Amino- 3,4-dihydro-2(1H)-phenanthrenone, hydrochloride

3-Amino-1-chloro-1,2,3,4-tetrahydro-2-phenanthrenol (103 mg) in trifluoroacetic acid (10 ml) was refluxed for 3 hours. The green mixture was evaporated and the residue was taken up in methanol and acidified with a solution of hydrochloric acid in diethyl ether. The evaporation residue was treated with charcoal in methanol. Filtration gave a clear solution which was evaporated to yield the crude compound as a solid (99 mg). Recrystallization from ethanol/diethyl ether afforded the title compound (40 mg) as a white solid, m.p. 247° C. (dec.).

EXAMPLE 6

(±)-3-amino-7-hexyl-3,4-dihydro-2(1H)-naphthalenone, hydrochloride

Step A: 1-(2-Nitroethenyl)-4-hexylbenzene

The title compound was prepared according to the procedure described in Example 3 step A. Starting from 4-hexylbenzaldehyde (12 g) a crude product was obtained as a brown solid. Recrystallization from acetic acid yielded the title compound (9.34 g) as a greenish solid.

Step B: 1-(2-Nitroethyl)-4-hexylbenzene

The title compound was prepared according to the procedure described in Example 3 step B. The reduction of 1-(2-nitroethenyl)-4-hexylbenzene with sodium borohydride gave an oil as the crude product; this oil was distilled at 180° C. under high vacuum (0.05 mBar) to afford the title compound as a brown liquid (5.93 g).

Step C:
α,αDiethoxymethyl-β-nitro-4-hexylbenzenepropanol

A mixture of 1-(2-nitroethyl)-4-hexylbenzene (5.86 g) glyoxal monodiethylacetal (1.64 g) and potassium carbonate (178 mg) was stirred under argon at 50° C. for 2½ hours. The mixture was diluted with diethyl ether (60 ml) and water was added (60 ml). The organic layer was separated and the aqueous layer was re-extracted with diethyl ether (3×30 ml). The combined organic layers were washed with saturated aqueous sodium chloride (100 ml) and dried over magnesium sulfate. Evaporation of solvent gave a residue which was purified by chromatography [silica gel 350 g, elution with ethyl acetate: cyclohexane, 1:9 (2 1) and 2:8 (2 1)]. The title compound was obtained as a yellow oil (3.42 g).

Step D:
α,α-Diethoxymethyl-β-tert-butoxycarbonylamino-4-hexylbenzenepropanol

A mixture of α,α-diethoxymethyl-β-nitro-4-hexylbenzenepropanol (2.31 g) and Raney nickel (0.6 g) in isopropanol (70 ml) was stirred under hydrogen at atmospheric pressure until the hydrogen absorption was complete. The mixture was degased in vacuo for 15 minutes and filtered through celite. Evaporation of solvent gave α, α-diethoxymethyl-B-amino-4-hexylbenzenepropanol (1.82 g) as an oil. This oil was reacted with di-tert-butyl-dicarbonate (1.19 g) in methanol (40 ml). The mixture was stirred at room temperature for 2 hours. The solvent was evaporated and the residue was purified by chromatography [silica gel 290 g, elution with ethyl acetate: cyclohexane, 2:8 (2 1)]. Two isomers of the title compound were isolated. Isomer A (0.90 g) and isomer B (0.90 g) were obtained as oils, Rf isomer A=0.30, Rf isomer B=0.19 (silica gel, ethyl acetate: cyclohexane, 1:4).

Step E:
3-Amino-7-hexyl-3.4-dihydro-2(1H)-naphthalenone, hydrochloride

A solution of α,α-diethoxymethylβ-tert-butoxycarbonylamino-4-hexylbenzenepropanol (170 mg) in trifluoroacetic acid (100 ml) was refluxed for 2 hours. The mixture was evaporated under reduced pressure, the residue was taken up in methanol and filtered. Evaporation gave a brown oil which was reacted again in refluxing trifluoroacetic acid (100 ml) for 1 hour. The mixture was evaporated. The residue dissolved in methanol was acidified with a solution of hydrochloric acid in diethyl ether and the mixture was evaporated. The acidification process was repeated twice. The residue was dried in vacuo to yield a brown solid (56 mg).

EXAMPLE 7

3-Amino-3,4-dihydro-6,8-dimethoxy-2(1H)-naphthalenone, hydrochloride

Step A: 1-(2-Nitroethenyl)-3,5-dimethoxybenzene

A mixture consisting of 3,5-dimethoxybenzaldehyde (20 g), nitromethane (20 ml), ammonium acetate (8 g) and acetic acid (80 ml) was refluxted for 1½ hours and the reaction mixture was poured into ice water. The yellow solid which separated was filtered and dried under high vacuum to yield the title compound (22.3 g).

Step B: 1-(2-Nitroethyl)-3.5-dimethoxybenzene

To a well stirred suspension of sodium borohydride (5 g) in a mixture of dioxane (100 ml) and absolute ethanol (30 ml) was added dropwise a solution of 1-(2-nitroethenyl)-3,5-dimethoxybenzene (12.6 g) in dioxane (100 ml) over a 100 ml) over a 1 hour period. Following addition the mixture was stirred for an additional 45 minutes period. To the resulting suspension were added ice-water (120 ml) and 50% aqueous acetic acid (10 ml). Agitation was maintained for 1 hour and the clear solution was concentrated under reduced pressure. The residue was extracted with ethyl acetate/water, the organic layer was washed with saturated aqueous sodium chloride and dried over magnesium sulfate. Evaporation of solvents afforded the crude title compound (10.8 g). Trap to trap distillation under high vacuum (0.05 Millibars) at 180° C. yielded 1-(2-nitroethyl)-3,5-dimethoxybenzene as a colorless oil (6.8 g).

Step C: α,α-Diethoxymethyl-β-nitro-3,5-dimethoxybenzenepropanol

A mixture of 1-(Z-nitroethyl)-3,5-dimethoxybenzene (6.68 mg), of glyoxal monodiethyl acetal (2.07 g) and of potassium carbonate (0.216 g) was stirred at 50° C. for 4 hours. The reaction mixture was diluted with diethyl ether, washed with water (2×50 ml) and saturated aqueous sodium chloride (50 ml). After drying over magnesium sulfate the organic solution was evaporated under reduced pressure to afford a residue which was purified on silica gel [180 g. elution with ethyl acetate:-cyclohexane, 1:9 (1 1), 1:4 (1 1)]. After evaporation of solvents the title compound was obtained as an oil (2.41 g).

Step D: α,α-Diethoxymethyl-β-amino-3.5-dimethoxybenzenepropanol

α,α-Diethoxymethyl-B-nitro-3,5-dimethoxybenzenepropanol (3.39 g) was hydrogenated in isopropanol (50 ml) over Raney nickel at atmospheric pressure and room temperature. When hydrogen absorption was complete, the reaction mixture was degased for 15 minutes under vacuum and the catalyst was filtered on celite. The solvent was evaporated under vacuum to yield the title compound as an oil (2.38 g).

Step E: α,α-Diethoxymethyl-β-tert-butoxycarbonylamino-3.5-dimethoxybenzene propanol α,α-diethoxymethyl-β-amino-3,5-dimethoxybenzenepropanol (2.38 g) was reacted with di-tert-butyl-dicarbonate (1.82g) in methanol (30 ml) for 1 hour at room temperature. The solvent was evaporated under vacuum and the residue was purified by chromatography on silica gel [130 g, elution with ethyl acetate:cyclohexane, 1:9–0.7 1), 1:4 (1 1) and 3:7(1 1)]. Two isomers of the title compound were isolated, isomer A as an oil (0.98 g) and isomer B (0.53 g) that could be crystallized from pentane, m.p. 73.5–75° C. RF isomer A=0.33, $R_F$ isomer B=0.20 (silica gel, ethyl acetate: cyclohexane, 3:7).

Step F: 3-amino3.4-dihydro-6.8-dimethoxy-2(1H)-naphthalenone. hydrochloride

α,α-Diethoxymethyl-β-tert-butoxycarbonylamino-3,5-dimethoxy-benzenepropanol (200 g) was dissolved in aqueous 37% hydrochloric acid (20 ml) cooled at 0° C. The resulting red solution was warmed at 100° C. for 3 minutes and then immediate ly cooled at 0° C. Evaporation of the reaction mixture yielded a brown solid which was recrystallized from an ethyl acetate/methanol mixture to give the title compound as a brown solid (101 mg).

EXAMPLE 8

Amino-1-fluoro-3.4-dihydro-2(1H)-naphthalenone hydrochloride (cis-chlorohydrin approach)

Step A: β-Nitro-α,α-(diethoxymethyl)benzenepropanol

Under argon a mixture of 1-nitro-2-phenylethane (18.11 g), glyoxal monodiethylacetal (12.23 g) and potassium carbonate (1.26 g) was stirred at 50–55° C. for 6 hours. The mixture was then diluted with diethyl ether, washed with water and saturated aqueous sodium chloride and dried over magnesium sulfate. The solvent was removed at reduced pressure and the crude material was purified on silica gel (500 g. elution with ethyl acetate: cyclohexane, 15:85) to give the title compound (22.08 g) as a yellow oil.

Step B: β-Tert-butoxycarbonylamino-α,α-(diethoxymethyl)-benzenepropanol

β-Nitro-α,α-(diethoxymethyl)benzenepropanol (14.7 g) and Raney nickel in 2-propanol (300 ml) were stirred at room temperature under hydrogen at atmospheric pressure. When hydrogen absorption was complete the mixture was degased in vacuo for 15 minutes and filtered through celite using propanol. The solvent was evaporated in vacuo to yield β-aminoα,α-(dIethoxymethyl)benzenepropanol (12.88 g) as an oil.

Di-tert-butyl-dicarbonate (12 g) was added to a solution of β-amino-α,α-(diethoxymethyl)benzenepropanol (12.88 g) in methanol (100 ml). The mixture was stirred for 5 hours at room temperature and the solvent was evaporated in vacuo. The residue was chromatographed [silica gel, 1 kg, elution with cyclohexane:ethyl acetate mixtures, 95:5 (1 1), 9:1 (2 1), 8:2 (2 1) and 7:3 (6 1)]. Two isomers of the title compound were isolated as oils, isomer A (6.41 g) and isomer B (4.30 g), Rf isomer A=0.26, Rf isomer B=0.21 (silica gel, ethyl acetate: hexane, 1:3).

Step C: (±)-(1R,2S,3R)-3-Amino-1-chloro-1,2,3,4-tetrahydro-2-naphthalenol, hydrochloride (amino-cis-chlorohydrin)

β-Tert-butoxycarbonylamino-α,α-(diethoxymethyl)-benzenepropanol, isomer A (4.213 g) was stirred in 37% aqueous hydrochloric acid (40 ml) at 0° C. for 45 minutes and at 100° C. for 3 minutes. The mixture was cooled in an ice bath. The precipitate was filtered, washed with water and dried in vacuo to afford the title compound (1.477 g) as a white solid, m.p. 189° C. (dec.).

Step D:
(±)-(1R,2S,3R)-3-Tert-butoxycarbonylamino-1-chloro-1,2,3,4-tetrahydro-2-naphthalenol (BOC-amino-cis-chlorohydrin)

To a well stirred mixture of di-tert-butyl-dicarbonate (720 mg) and (±)-(1R,2S,3R)-3-amino1-chloro-1,2,3,4-tetrahydro-2-naphthalenol hydrochloride (710mg) in methanol (15 ml) was added dropwise a solution of triethylamine (390 mg) in methanol (10 ml). Stirring was maintained for 3 hours at room temperature and the mixture was evaporated under reduced pressure. The residue was taken up into methylene chloride, the organic solution was washed with water, saturated aqueous sodium chloride and dried over magnesium sulfate. Evaporation of solvent afforded a residue which was recrystallized from an hexane/diethyl ether mixture to yield the title compound (340 mg) as a white solid.

Step E: (±)-(1S, 2S, 3R)-3-Tert-butoxycarbonylamino-1-fluoro-1,2,3,4-tetrahydro-2-naphthalenol A mixture of (±)-1R,2S,3R)-3-tert-butoxycarbonylamino-1-chloro-1,2,3,4-tetrahydro-2-naphthalenol (196mg) and AMBERLYST A-26F resin (1.04 g) in hexane (10 ml) was refluxed for 4 hours. The resin was filtered and washed with warm hexane. The filtrate was evaporated in vacuo and the residue was chromatographed (silica gel 20g, elution with cyclohexane:ethyl acetate, 4:1) to afford the title compound (24 mg) as an oil.

Step F:
3-Tert-butoxycarbonylamino-1-fluoro-3,4-dihydro-2(1H)-naphthalenone

To a solution of (±)-(1S,2S,3R)-3-tert-butoxycarbonylamino-1-fluoro-1,2,3,4-tetrahydro-2-naphthalenol (140mg) in anhydrous methylene chloride (5 ml) was added Dess-Martin periodinane (340 mg) and tert-butyl-alcohol (70 mg). Stirring was maintained at room temperature for 3½ hours. The reaction was quenched with isopropanol and the reaction mixture was poured on a silica gel column (50 g, elution with cyclohexane: ethyl acetate, 9:1) to afford the title compound (105 mg) as an oil. Step G: 3-Amino-1-fluoro-3,4-dihydro-2(1H)-naphthalenone, hydrochloride Under argon 3-tert-butoxycarbonylamino-1-fluoro-3,4-dihydro-2(1H)-naphthalenone (105 mg) was treated with a saturated solution of hydrochloric acid in diethyl ether for 2½ hours. The solid which precipitated out was filtered and dried in vacuo to yield the title compound as a white solid (65 mg).

EXAMPLE 9

3Amino1-fluoro-3,4-dihydro-2(1H)-naphthalenone, hydrochloride (trans-chlorohydrin approach)

Step A:
(±)-(1R,2R,3R)-3-Amino-1-chloro-1,2,3,4-tetrahydro-2-naphthalenol. hydrochloride (amino-trans-chlorohydrin)

β-Tert-butoxycarbonylamino-α,α-(diethoxymethyl)-benzenepropanol isomer B (4.3 g) was treated as in Example 8 step C to yield the title compound (1.53 g) as a white solid, m.p. 198° C. (dec.).

Step B:
(±)-(1R,2R,3R)-3-Tert-butoxycarbonylamino-1-chloro-1,2,3,4-tetrahydro-2-naphthalenol (BOC-amino-trans-chlorohydrin)

To a well stirred mixture of (±)-(1R,2R,3R)-3-amino-1-chloro-1,2,3,4-tetrahydro-2-naphthalenol, hydrochloride (1 g) and di-tert-butyl-dicarbonate (1 g) in methanol (20 ml) was added dropwise a solution of triethylamine (0.43 g) in methanol (20 ml) over a period of 40 minutes. The mixture was stirred overnight at room temperature and evaporated in vacuo. The residue was crystallized from a hexane/diethyl ether mixture to give the title compound as a white solid.

Step C:
(±)-(1S,2R,3R)-3-Tert-butoxycarbonylamino-1.2-epoxy-1,2,3,4-tetrahydro-naphthalene A solution of (±)-(1R,2R,3R)-3-tert-butoxycarbonylamino-1-chloro-1,2,3,4tetrahydro-2-naphthalenol (348 mg) and 1,8-diazabicyclo[5.4.0]undec-7-ene (400 mg) in tetrahydrofuran (10 ml) was refluxed for 1½ hours. The mixture was diluted with methylene chloride, washed with saturated aqueous sodium chloride, dried over magnesium sulfate and concentrated in vacuo. The residue was recrystallized from cyclohexane (193 mg) to yield the title compound as a white solid, m.p. 118–119° C.

Step D:
(±)-(1R,2R,3R)-3-Tert-butoxycarbonylamino-1-fluoro-1,2,3,4-tetrahydro-2-naphthalenol To a solution of (±)-(1S,2R,3R)-3-tert-butoxycarbonylamino-1,2-epoxy-1,2,3,4-tetrahydro-naphthalene (100 mg) in anhydrous diethyl ether (6 ml) cooled in an ice-bath was added 70% hydrogen fluoride pyridine (0.24 ml). The mixture was stirred at 0° C. for 9 hours, ice was added and the reaction mixture was neutralized by addition of solid sodium bicarbonate (1.2 g) at 0° C. and extracted with diethyl ether. The organic layer was dried over magnesium sulfate and evaporated to afford the crude title compound as an oil (65 mg). This crude material was purified by chromatography on silica gel (10 g, elution with ethyl acetate:cyclohexane, 2:8) and the resulting material (35 mg) was crystallized from a diethyl ether/pentane mixture to afford the title compound as a white solid, m.p. 98–99° C.

Step E:
3-Tert-butoxycarbonylamino-1-fluoro-3,4-dihydro-2(1H)naphthalenone

As in Example 8, Step F.

Step F:
3-Amino-1-fluoro-3,4-dihydro-2(1H)-naphthalenone, hydrochloride

As in Example 8, Step G.

EXAMPLE 10

1-Isoamylamino-3-amino-3,4-dihydro-2(1H)-naphthalenone, dihydrochloride

STEP A:
(±)-(1S,2R,3R)-1-Isoamylamino-3-tert-butoxycarbonylamino-1,2,3,4-tetrahydro-2-naphthalenol Under argon a solution of (1R,2S,3R)-3-tert-butoxycarbonylamino-1-chloro-1,2,3,4-tetrahydro-2-naphthalenol (BOC-amino-cis-chlorohydrin) (500 mg) in anhydrous tetrahydrofuran was refluxed with isoamylamine (1.0 ml) and triethylamine (250 μl) for 5 hours at 90° C. The mixture was poured in aqueous 5% sodium bicarbonate and extracted with methylene chloride. The organic solution was dried over magnesium sulfate and evaporated under vacuum to yield an oil. Crystallization of this oil in hexane yielded the title compound as a white solid (270 mg).

Step B:
(±)-(1S,2S,3R)-N$^1$,N$^3$-Bis(tert-butoxycarbonyl)-N$^1$-isoamyl-1,3-diamino-1,2,3,4tetrahydro-2-naphthalenol (±)-(1S,2R,3R)-1-isoamylamino-3-tert-butoxycarbonyl-amino-1,2,3,4-tetrahydro-2-naphthalenol (200 mg) was treated with di-tert-butyl-dicarbonate (170 mg) in methanol (5 ml) for 24 hours at room temperature. Evaporation of the reaction mixture under vacuum gave an oil which was filtered through silica gel (elution with cyclohexane:ethyl acetate, 4:1) to yield the title compound as an oil (150 mg).

Step C:
N$^1$,N$^3$Bis(tert-butoxycarbonyl)-N$^1$-isoamyl-1,3-diamino-3,4-dihydro-2(1H)-naphthalenone Under argon to a solution of (±)-(1S,2S,3R)-N$^1$,N$^3$-bis-(tert-butoxycarbonyl) -N$^1$-isoamyl-1,3-diamino-1,2,3,4-tetrahydro-2-naphthalenol (140 mg) in anhydrous methylene chloride (5 ml) was added Dess-Martin periodinane (230 mg) at room temperature. After 1 hour stirring at room temperature the reaction mixture was filtered through silica gel (elution with cyclohexane:ethyl acetate, 9:1) to yield the title compound as 6 an oil (100 mg).

Step D:
1-Isoamylamino-3-amino-3,4-dihydro-2(1H)-naphthalenone, dihydrochloride

Under argon N$^1$,N$^3$-bis(tert-butoxycarbonyl)-N$^1$-isoamyl-1,3-diamino-3,4-dihydro-2(1H)-naphthalenone (90 mg) was dissolved into a saturated solution of hydrochloric acid in diethyl ether. The mixture was stirred for 6hours at room temperature. The precipitate was decanted from the etheral solution and dried under vacuum. The title compound was obtained as a white solid (50 mg).

EXAMPLE 11

3-Amino-3,4-dihydro-1-isopropyloxy-2(1H)-naphthalenone, hydrochloride

Step A:
1R,2R,3R)-3-Tert-butoxycarbonylamino-1,2,3,4-tetrahydro-1-isopropyloxy-2-naphthalenol Under argon to a solution of (±)-(1S,2R,3R)-3-tert-butoxycarbonylamino -1,2-epoxy-1,2,3,4-tetrahydronaphthalene (96 mg) in methanol (4 ml) was added titanium isopropoxyde (0.19 ml). The mixture was warmed for 14 hours in an oil bath maintained at 96° C. Evaporation of the warm mixture under an argon flow gave a residue which was purified on a silica gel column (22 g, elution with ethyl acetate:cyclohexane, 1:4). After evaporation of solvents was recovered an oil which was crystallized from a pentane/diethyl ether mixture to afford the title compound as a white solid (56 mg).

Step B:
3-Tert-butoxycarbonylamino-3,4-dihydro-1-isopropyloxy-2(1H)-naphthalenone Under argon to a solution of (±)-(1R,2R,3R)-3-tert-butoxycarbonylamino -1,2,3,4-tetrahydro-1-isopropyloxy-2-naphthalenol (50 mg) in anhydrous methylene chloride (4 ml) was added Dess-Martin periodinane (100 mg). Agitation was maintained at room temperature for 2 hours. The reaction mixture was filtered on a silica gel column (10 g, elution ethyl acetate:cyclohexane, 1:9) to afford the title compound as an oil (38 mg).

Step C:
3-Amino-3,4-dihydro-1-isopropyloxy-2(1H)naphthalenone, hydrochloride

Under argon 3-tert-butoxycarbonylamino-3,4-dihydro-1-isopropyloxy-2(1H)-naphthalenone (30 mg) was dissolved in formic acid (1 ml) and the mixture was set aside at room temperature for 4 hours. Formic acid was evaporated under vacuum and the residue was acidified with aqueous 0.01N hydrochloric acid. Evaporation of the mixture and recrystallization of the residue in an ethyl acetate/methanol mixture yielded the title compound as a white solid (20 mg).

EXAMPLE 12

3-Amino-3,4-dihydro-1-methyl-2(1H) naphthalenone. hydrochloride

Step A:
(±)-(1R,2S,3R)-3-Tert-butoxycarbonylamino-1,2,3,4-tetrahydro-1-methyl-2-naphthalenol Under argon to a solution of (±)-(1S,2R,3R)-3-tert-butoxycarbonylamino -1,2-epoxy-1,2,3,4-tetrahydronaphthalene (108 mg) in hexane (10 ml) was added a 2 M solution of trimethylaluminum in hexane (0.30 ml), the mixture was heated under reflux for 3½ hours and was quenched by addition of a 2 M aqueous solution of ammonium chloride adjusted to pH 8 with ammonium hydroxide. The resulting suspension was extracted with ethyl acetate. The ethyl acetate solution was dried over magnesium sulfate and evaporated under vacuum to give a colorless oil which was purified by preparative thin layer chromatography on silica gel (elution with ethyl acetate:cyclohexane, 3:8) to afford the title compound as a solid (32 g).

Step B:
3-Tert-butoxycarbonylamino-3,4-dihydro-1-methyl-2(1H)-naphthalenone

The oxidation of (±)-(1R,2S,3R)-3-tert-butoxycarbonylamino -1,2,3,4-tetrahydro-1-methyl-2-naphthalenol was performed as in Example 11, Step B.

Step C:
3-Amino-3,4-dihydro-1-methyl-2(1H)-naphthalenone. hydrochloride

The BOC deprotection was achieved in a solution of hydrochloric acid in diethyl ether as described in Example 8, Step G.

EXAMPLE 13

3-Amino-1,1-difluoro-3,4-dihydro-2(1H)-naphthalenone hydrochloride

Step A:
(±)(1R,2S,3R)-3-Benzoylamino-1-chloro-1,2,3,4-tetrahydro-2-naphthalenol To a mixture of (±)-(1R,2S,3R)-3-amino-1-chloro-1,2,3,4-tetrahydro-2-naphthalenol (547 mg) in water (10 ml) and benzoylchloride (367 mg) in toluene (6 ml) was added dropwise a solution of sodium bicarbonate (420 mg) in water (10 ml) over a period of 30 minutes. Stirring was maintained at room temperature for an additional period of 30 minutes. The mixture was extracted with chloroform, washed with saturated aqueous sodium chloride and evaporated in vacuo. Recrystallization of the residue from a cyclohexane/ethyl acetate mixture yielded the title compound (357 mg) as a white solid.

Step B:
(±)-(3aR,9R,9aR)-9-Chloro-3a,4,9,9a-tetrahydro-2-phenyl-naphth[2,3-d]oxazole (±)-(1R,2S, 3R)-3-Benzoylamino-1-chloro-1,2,3,4-tetrahydro-2-naphthalenol (204 mg) in thionyl chloride as solvent was stirred at 50° C. for 2 hours. Evaporation of thionyl chloride gave a solid residue which was triturated in warm ethyl acetate and filtered to yield the title compound (151 mg) as a white solid.

Step C:
(±)-(3aR,9aR)-3a,4,9,9a-Tetrahydro-2-phenyl-naphth[2,3d]oxazol-9-ol

To a solution of (±)-(3aR,9R,9aR)-9-chloro-3a,4,9-,9a-tetrahydro-2-phenyl-naphth[2,3-d]oxazole (360 mg) in 2-methoxyethanol (10 ml) was added a solution of lithium hydroxyde monohydrate (67 mg) in water (2 ml). The mixture was warmed at 90° C. for ½ hour and the title compound was precipitated by addition of water. Filtration, washing with water and drying in vacuo gave the title compound as a yellow solid (205 mg).

Step D:
(±)-(3aR,9aR)-3a,4-Dihydro-2-phenyl-naphth-[2,3-d]-oxazol-9(9aH)-one Under argon to a solution of (±)-(3aR,9aR)-3a,4,9-,9a-tetrahydro-2-phenyl-naphth-[2,3-d]oxazol 9-ol in methylene chloride (10 ml) was added Dess Martin periodinane (640 mg) and tert-butylalcohol (56 mg). After 5 hours stirring at room temperature, isopropanol was added and the reaction mixture was filtered on a silica gel column (elution with cyclohexane: ethyl acetate, 40:1). Evaporation of solvents gave the title compound as an oil (150 mg).

Step E:
(±)-(3aR,9aR)-9,9-Difluoro-3a,4,9,9a-tetrahydro-2-phenyl-naphth[2,3-d]oxazole To a solution of (±)-(3aR,9aR)-3a,4-dihydro-2-phenyl-naphth[2,3 d]oxazol-9(9aH)-one (100 mg) in methylene chloride (10 ml) was added diethylaminosulfur trifluoride (100 µl). The mixture was stirred for 24 hours at room temperature and pour ed into ice water. The organic layer was washed with saturated aqueous sodium chloride and dried over magnesium sulfate. The solvent was evaporated in vacuo and the residue was crystallized in a cyclohexane/ethyl acetate mixture to yield the title compound 55 mg).

Step F:
(±)-(2R,3R)-3-Amino-1,1-difluoro-1,2,3,4-tetrahydro-2-naphthalenol, hydrochloride A suspension of (±)-(3aR,9aR)-9,9-difluoro-3a,4,9-,9a-tetrahydro-2-phenyl-naphth[2,3-d]oxazole (50 mg) in 2.5 N aqueous hydrochloric acid was refluxed overnight. The mixture was concentrated in vacuo and the residue was crystallized from water. Benzoic acid was filtered and the filtrate was concentrated to afford the crude product which was recrystallized from methanol-/ethyl acetate affording the title compound (35 mg).

Step G:
(±)-(2R,3R)-3-Tert-butoxycarbonylamino-1,1-difluoro-1,2,3,4-tetrahydro-2-naphthalenol A mixture of (±)-(2R,3R)-3-amino-1,1-difluoro-1,2,3,4-tetrahydro-2-naphthalenol hydrochloride (50 mg), di-tert-butyl-dicarbonate (50 mg) and triethylamine (25 mg) in methanol (2 ml) was stirred at room temperature for 4 hours. The mixture was concentrated in vacuo and the residue was crystallized from a cyclohexane/ethyl acetate mixture to yield the title compound (45 mg).

Step H:
3-Tert-butoxycarbonylamino-1,1-difluoro-3,4-dihydro-2(1H)-naphthalenone 3-Tert-butoxycarbonylamino-1,1-difluoro-1,2,3,4-tetra-hydro-2-naphthalenol was oxidized to the title compound by the procedure described in Example 8, Step F.

Step I: 3-Amino-1,1-difluoro-3,4-dihydro-2(1H)-naphthalenone, hydrochloride

Deprotection of (±)-3-tert- butoxycarbonylamino-1,1-difluoro-3,4-dihydro-2(1H) naphthalenone was achieved using the procedure described in Example 8, Step G to yield the title compound.

EXAMPLE 14

3-Amino-octahydro-2(1H)-naphthalenone, hydrochloride

Step A:
3-Tert-butoxycarbonylamino-decahydro-2-naphthalenol

A solution of 3-tert-butoxycarbonylamino-1,2,3,4-tetra-hydro-2-naphthalenol (1.05 g) in acetic acid (100 ml) was hydrogenated over platinum oxyde (121 mg) under pressure (5.5.6 bars) at room temperature for 3 days. The catalyst was filtered and the solvent was evaporated under vacuum. The residue was purified by chromatography on silica gel [140 g, elution with ethyl acetate:cyclohexane, 2:8 (0.7 1) and 5:7 (1 1)]to afford the title compound as an oil (915 mg).

Step B: 3-Tert-butoxycarbonylamino octahydro-2(1H)-naphthalenone

Under argon to a solution of 3-tert-butoxycarbonylaminodecahydro-2-naphthalenol (0.27 g) in methylene chloride (5 ml) was added pyridinium dichromate (572 mg), molecular sieves 3A powder (791 mg) and acetic acid (100 µl). The reaction mixture was stirred for 50 minutes at room temperature. The black mixture was filtered through a silica gel column (60 g, elution with ethyl acetate:cyclohexane, 1:4) to give, after evaporation of solvents, the title compound as a viscous oil (165 mg).

Step C: 3-Amino-octahydro-2(1H)-naphthalenone, hydrochloride

Under argon 3-tert-butoxycarbonylamino-decahydro-2-naphthalenone (165 mg) was treated with a saturated solution of hydrochloric acid in diethyl ether (10 ml). The mixture was left aside for 24 hours, a precipitate was formed. The super natant was discarded and the solid washed with anhydrous diethyl ether to yield the title compound as a yellow solid (90 mg). It was recrystallized from a cyclohexane/ethyl acetate/methanol mixture to afford the title compound as a white solid.

The compounds of Formula I, and the pharmaceutically acceptable salts thereof, can be administered to a mammalian specie (e.g., humans) as an analgesic agent due to their ability to inhibit an enkephalin-degrading aminopeptidase.

It is well known that the weak and shortlasting analgesic activity of endogenous enkephalins can be attributed to their rapid inactivation. Enkephalins are metabolized by several hydrolytic enzymes present in the brain: (1) aminopeptidases release the $Tyr^1$ residue, (2) a dipeptidyl aminopeptidase releases the $Tyr^1$-$Gly^2$ residue and (3) two enzymes cleave the penultimate $Gly^3$-$Phe^4$ bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the aminopeptidase activity and thus act as analgesic agents.

In addition to their use as analgesic agents, the compounds of this invention (I) are also useful as agents which may be used in conjunction with known therapeutic agents. For example, aminopeptidase inhibitors (such as bestatin) are known to exert an immunomodulating effect and therefore have been found to be useful in the conjunctive therapy with agents useful in the treatment of such diseases as cancer and acquired immuno deficiency syndrom. Indeed, compounds of this invention have been found to potentiate the effect of natural killer cells.

Using standard in vitro and in vivo assays designed to demonstrate aminopeptidase inhibiting properties and end-use applications (respectively) as well as by comparative tests with aminopeptidase inhibitors known to have been useful in exerting beneficial end-use applications, the compounds of this invention exert their beneficial effects at a daily dose of about 0.1 mg to about 25 mg of compound per kilogram of body weight.

A compound of Formula I, or a pharmaceutically acceptable salt thereof, can be administered to patients orally or parenterally in an effective amount within the daily dosage range of about 0.1 to about 25 mg of compound per kilogram of patient body weight. Administration is preferably in 2 to 4 divided doses and compounds may be administered enterally or parenterally in accordance with the condition of the patient being treated using pharmaceutical formulations according to techniques well known in the art.

As is true for most generic classes of compounds which are suitable for use as chemotherapeutic use, certain subgeneric groups and certain specific compounds are preferred. In this instance, those compounds of Formula I wherein the dotted lines represent a facultative double bond are preferred over their saturated analogs, compounds wherein $R_1$ is H and $R_2$ is H, F, Cl are most preferred with alkyl, alkoxy, alkylamino, acyloxy or acylamino being other preferred $R_2$ moieties when $R_1$ is H, and when $R_1$ is other than H, then it is preferred that both $R_1$ and $R_2$ be fluoro, chloro or alkyl. When $R_6$, $R_7$ and $R_9$ are H, it is preferred that $R_8$ be H, alkyl, alkoxy, alkylamino or alkylthio. When any of the $R_7$ and $R_8$, $R_8$ and $R_9$, or $R_6$ and $R_7$ combinations together with the carbon atoms to which they are attached, form a benzene ring then it is preferred that $R_6$ and $R_9$, $R_6$ and $R_7$, and $R_8$ and $R_9$, respectively, be H. Preferred compounds of this type are the $R_1$ and $R_2$ substituted or unsubstituted 3-amino-3,4-dihydro-2(1H)phenanthrenones and the 2-amino-1,2-dihydro-3(4H)phenanthrenones. When the dotted lines of the compounds of Formula I represent a saturated ring (thereby forming the decalin analogs of the unsaturated compounds) it is preferred that all the $R_6$ to $R_9$ substituents be hydrogen or that one be alkyl. When $R_1$ and $R_2$ are H and substituents are present on the benzenoid moiety. it is preferred that such substituents be 7,9-dimethoxy, 7,9-dichloro. or 7,9-dihydroxy. Preferred specific compounds are those wherein $R_1$ and $R_2$ are H,H, or F,F, Cl,Cl, or H,F, or H,Cl whilst $R_6$, $R_7$, $R_8$ and $R_9$ are H, or $R_8$ is hexyl, or $R_7$ and $R_9$ are dimethoxy, or dichloro, or dihydroxy, or $R_6$ and $R_7$, together with the carbon atoms to which they are attached, form a 3-amino-3,4-dihydro-2(1H)phenanthrenone, or when $R_8$ and $R_9$, together with the carbon atoms to which they are attached, form a 2-amino-1,2-dihydro-3(4H)phenanthrenone. Other preferred compounds are those wherein $R_2$ is methyl, isopropoxy or isoamylamino whilst $R_1$, $R_6$, $R_7$, $R_8$ and $R_9$ are H. Of course, the foregoing specific :compounds are compounds wherein the dotted lines of Formula I represent double bonds.

We claim:

1. A method of treating a patient in need of analgesic relief which comprises administering to said patient an effective analgesic amount of a compound having the formula;

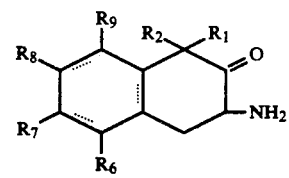

the enantiomeric forms and mixtures thereof, and the pharmaceutically acceptable salts thereof wherein the dotted lines represent facultative double bonds, $R_1$ is H, F, Cl, $C_{1-6}$ alkyl, OH, $C_{1-6}$ alkoxy, $C_{1-6}$ alkyl thio, $C_{1-6}$ acylamino, or $C_{1-6}$ acyloxy; $R_2$ is H, Cl, F or $C_{1-6}$ alkyl; each of $R_6$, $R_7$, $R_8$ and $R_9$ is H, Cl, F, $C_{1-6}$ alkyl, $C_{1-6}$ alkylamino, $C_{1-6}$ alkoxy, aryl or aralkyl; and when $R_6$ and $R_7$, $R_7$ and $R_8$, and $R_8$ and $R_9$ are taken together with the carbon atoms to which they are attached form a 5-6 membered carbocyclic moiety, with the proviso that the number of so-formed carbocyclic moieties is limited to less than 3, and with the further proviso that when the depicted ring moiety having the facultative double bonds is saturated then any 5-6 membered carbocyclic moiety formed therewith is also saturated.

2. A method according to claim 1 wherein $R_1$ is H, F, Cl, $C_{1-6}$ alkyl, OH or $C_{1-6}$ alkoxy; $R_2$ is H, Cl, F or $C_{1-6}$ alkyl; each of $R_6$, $R_7$, $R_8$ and $R_9$ is H, Cl, F or $C_{1-6}$ alkyl; and when $R_6$ and $R_7$, $R_7$ and $R_8$, and $R_8$ and $R_9$ are taken together with the carbon atoms to which they are attached, they form a 6-membered carbocyclic moiety with the proviso that when the depicted ring moiety having the facultative double bonds is saturated $R_1$, $R_2$, $R_6R_7,R_8$, and $R_9$ cannot all be hydrogen, and with the further proviso that when the depicted ring moiety having the facultative double bonds is saturated then the 6-membered carbocyclic moiety formed is also saturated.

3. A method according to claim 1 wherein $R_1$ and $R_2$ are hydrogen.

4. A method according to claim 1 wherein $R_6$, $R_7$, $R_8$ and $R_9$ are hydrogen.

5. A method according to claim 1 wherein $R_6$ and $R_7$, together with the carbon atoms to which they are attached, form a 3-amino-1,2-dihydro-2(1H)phenanthrenone.

6. A method according to claim 1 wherein $R_8$ and $R_9$, together with the carbon atoms to which they are attached, form a 2-amino-1,2-dihydro-3(4H)phenanthrenone.

7. A pharmaceutical composition comprising having a therapeutically effective amount of a compound having the formula

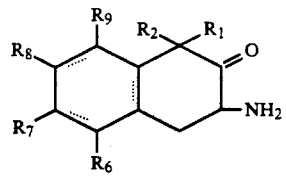

I

The enantiomeric forms and mixtures thereof, and the pharmaceutically acceptable salts thereof wherein the dotted lines represent facultative double bonds, $R_1$ is H, F, Cl, $C_{1-6}$ alkyl, OH, $C_{1-6}$ alkyl thio, $C_{1-6}$ acylamino, or $C_{1-6}$ acyloxy; $R_2$ is H, Cl, F or $C_{1-6}$ alkyl; each of $R_6$, $R_7$, $R_8$ and $R_9$ is H, Cl, F, $C_{1-6}$ alkyl, $C_{1-6}$ alkylamino, $C_{1-6}$ alkoxy, aryl or aralkyl; and when $R_6$ and $R_7$, $R_7$ and $R_8$, and $R_8$ and $R_9$ are taken together with the carbon atoms to which they are attached form a 5–6 membered carbocyclic moiety, with the proviso that the number of so-formed carbocyclic moieties is limited to less than 3, and with the further proviso that when the depicted ring moiety having the facultative double bonds is saturated then any 5–6 membered carbocyclic moiety formed therewith is also saturated in combination with a pharmaceutically acceptable carrier.

8. A pharmaceutical composition comprising having a therapeutically effective amount of a compound having the formula $R_1$ is H, F, Cl, $C_{1-6}$ alkyl, OH or $C_{1-6}$ alkoxy, $R_2$ is H, Cl, F or $C_{1-6}$ alkyl, each of $R_6$, $R_7$, $R_8$ and $R_9$ is H, Cl, F or $C_{1-6}$ alkyl, and when $R_6$ and $R_7$, $R_7$ and $R_8$, and $R_8$ and $R_9$ are taken together with the carbon atoms to which they are attached, they form a 6-membered carbocyclic moiety with the proviso that when the depicted ring moiety having the facultative double bonds is saturated $R_1$, $R_2$, $R_6$, $R_7$, $R_8$, and $R_9$ cannot all be hydrogen, and with the further proviso that when the depicted ring moiety having the facultative double bonds is saturated then the 6-membered carbocyclic moiety formed is also saturated in combination with a pharmaceutically acceptable carrier.

* * * * *